US009566017B2

(12) United States Patent
Kummer

(10) Patent No.: US 9,566,017 B2
(45) Date of Patent: Feb. 14, 2017

(54) METHOD AND APPARATUS FOR IDENTIFYING A USER OF AN ELECTRONIC DEVICE USING BIOELECTRICAL IMPEDANCE

(75) Inventor: David A. Kummer, Highlands Ranch, CO (US)

(73) Assignee: EchoStar Technologies L.L.C., Englewood, CO (US)

( * ) Notice: Subject to any disclaimer, the term of this patent is extended or adjusted under 35 U.S.C. 154(b) by 2568 days.

(21) Appl. No.: 12/252,045

(22) Filed: Oct. 15, 2008

(65) Prior Publication Data

US 2010/0094157 A1 Apr. 15, 2010

(51) Int. Cl.
| | |
|---|---|
| *G05B 19/00* | (2006.01) |
| *A61B 5/053* | (2006.01) |
| *A61B 5/117* | (2016.01) |
| *A61B 5/00* | (2006.01) |
| *G06F 21/32* | (2013.01) |
| *H04H 60/45* | (2008.01) |

(52) U.S. Cl.
CPC ............ *A61B 5/053* (2013.01); *A61B 5/117* (2013.01); *A61B 5/6825* (2013.01); *A61B 5/6887* (2013.01); *G06F 21/32* (2013.01); *H04H 60/45* (2013.01); *G06F 2221/2149* (2013.01)

(58) Field of Classification Search
CPC ...... G06F 21/32; G06F 21/10; G06F 21/6209; G06F 9/4451; G06F 21/45; G06F 21/6245; H04N 21/4415; H04W 12/06
See application file for complete search history.

(56) References Cited

U.S. PATENT DOCUMENTS

| | | | |
|---|---|---|---|
| 2002/0179338 A1* | 12/2002 | Tanida et al. | 177/25.13 |
| 2002/0188854 A1* | 12/2002 | Heaven et al. | 713/186 |
| 2004/0019292 A1* | 1/2004 | Drinan et al. | 600/547 |
| 2005/0160458 A1* | 7/2005 | Baumgartner | 725/46 |
| 2006/0122533 A1 | 6/2006 | Park et al. | |
| 2006/0129333 A1* | 6/2006 | Ashida et al. | 702/30 |

(Continued)

OTHER PUBLICATIONS

"How BIA Works", excerpt from the Tanita internet site located at http://www.tanita.com/HowBIAworks.shtml, retrieved on Aug. 29, 2008, 1 page.

(Continued)

*Primary Examiner* — Kerri McNally
*Assistant Examiner* — Renee Dorsey
(74) *Attorney, Agent, or Firm* — Ingrassia Fisher & Lorenz, P.C.

(57) ABSTRACT

A method for identifying a user of an electronic device is presented. In the method, for each of a plurality of users, a bioelectrical impedance of the user is measured, a value based on the measurement is generated, and the value is associated with information corresponding to the user. A bioelectrical impedance of a current user of the electronic device is also measured, and a value based on this measurement is generated. The value associated with the current user is compared with at least one of the values associated with the plurality of users. In response to the comparison, the electronic device is operated based on the information corresponding to one of the plurality of users in response to the current user interacting with the electronic device if the value associated with the current user indicates the current user is the one of the plurality of users.

20 Claims, 8 Drawing Sheets

(56) References Cited

U.S. PATENT DOCUMENTS

| | | | |
|---|---|---|---|
| 2006/0176149 A1* | 8/2006 | Douglas | 340/5.74 |
| 2006/0241360 A1* | 10/2006 | Montagnino et al. | 600/310 |
| 2007/0030115 A1* | 2/2007 | Itsuji et al. | 340/5.8 |
| 2007/0143233 A1* | 6/2007 | Van Doren | 706/14 |
| 2007/0241861 A1* | 10/2007 | Venkatanna et al. | 340/5.52 |
| 2008/0001735 A1* | 1/2008 | Tran | 340/539.22 |
| 2008/0095409 A1* | 4/2008 | McQuaide | 382/115 |
| 2009/0146779 A1* | 6/2009 | Kumar et al. | 340/5.31 |

OTHER PUBLICATIONS

"Bioelectrical impedance analysis", excerpt from the Wikipedia internet site located at http://en.wikipedia.org/w/index.php?title=Bioelectrical_impedance_analysis&printable=yes, retrieved on Aug. 29, 2008, 1 page.

"Bioimpedance", excerpt from the Wikipedia internet site located at http://en.wikipedia.org/w/index.phptitle=Bioimpedance&printable=yes, retrieved on Mar. 17, 2008, 3 pages.

\* cited by examiner

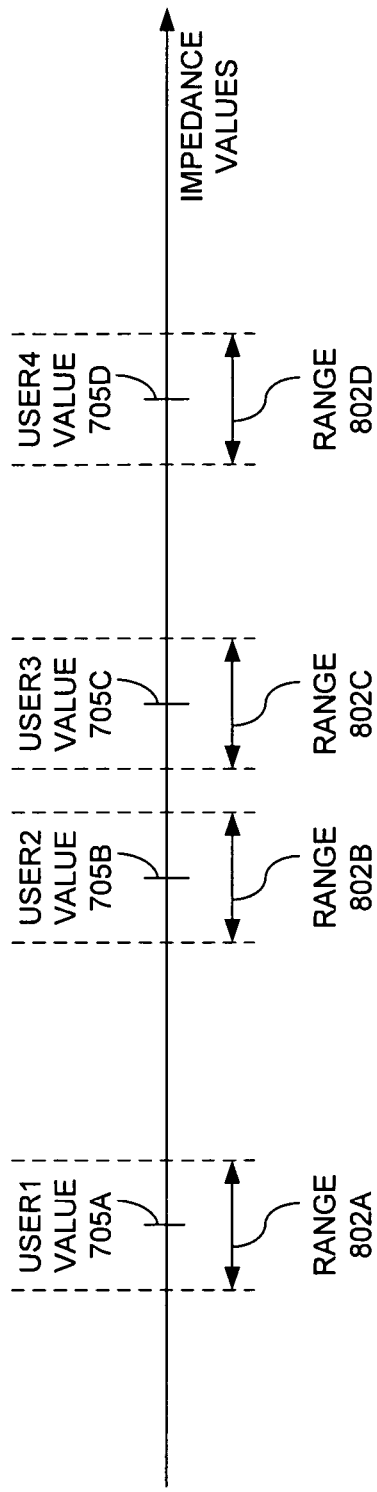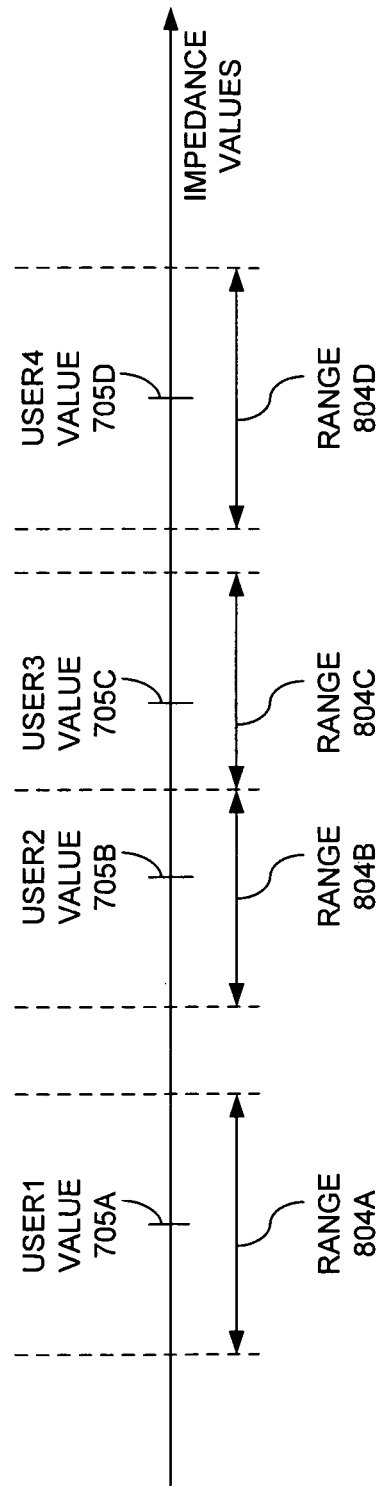

METHOD AND APPARATUS FOR IDENTIFYING A USER OF AN ELECTRONIC DEVICE USING BIOELECTRICAL IMPEDANCE

BACKGROUND

Identification of a user of an electronic device has long been either desirable or necessary, depending on the device and the particular environment in which the device is used. For example, access to a computer system or communication network is often strictly controlled or regulated, especially when the data accessible on such a system is of an extremely sensitive or confidential nature, such as corporate, financial, medical, or military records. Typically, the system being protected requires a prospective user to provide some proof of identity, such as a user name and/or password or other confidential data, before the user is granted to access the system.

Various circumstances, such as lost or forgotten passwords, stolen passwords, and other maladies, often lead to either an authorized user being denied access to a system, or an unauthorized user being granted access. Also, memorization and entry of user names and passwords, or other identifying information, is often considered tedious and overly time-consuming.

In response, alternative ways of securely identifying a user have been implemented or proposed. For example, the use of fingerprint scanners, retinal scanners, and similar devices which measure some user physical characteristic have been proposed to identify potential users to restrict access to a computer system to those authorized to do so. The use of such devices typically eliminates the need to enter a password or other identifying data, thus reducing the time required to access the secured system. However, some user-accessible systems may not involve the extremely sensitive or confidential data that warrant such intensive security measures.

BRIEF DESCRIPTION OF THE DRAWINGS

Many aspects of the present disclosure may be better understood with reference to the following drawings. The components in the drawings are not necessarily depicted to scale, as emphasis is instead placed upon clear illustration of the principles of the disclosure. Moreover, in the drawings, like reference numerals designate corresponding parts throughout the several views. Also, while several embodiments are described in connection with these drawings, the disclosure is not limited to the embodiments disclosed herein. On the contrary, the intent is to cover all alternatives, modifications, and equivalents.

FIG. 8A is a graphical representation of acceptable ranges of measured bioelectrical impedance for each of several users according to an embodiment of the invention.

FIG. 8B is a graphical representation of acceptable ranges of measured bioelectrical impedance for each of several users according to another embodiment of the invention.

DETAILED DESCRIPTION

The enclosed drawings and the following description depict specific embodiments of the invention to teach those skilled in the art how to make and use the best mode of the invention. For the purpose of teaching inventive principles, some conventional aspects have been simplified or omitted. Those skilled in the art will appreciate variations of these embodiments that fall within the scope of the invention. Those skilled in the art will also appreciate that the features described below can be combined in various ways to form multiple embodiments of the invention. As a result, the invention is not limited to the specific embodiments described below, but only by the claims and their equivalents.

Figure 1:
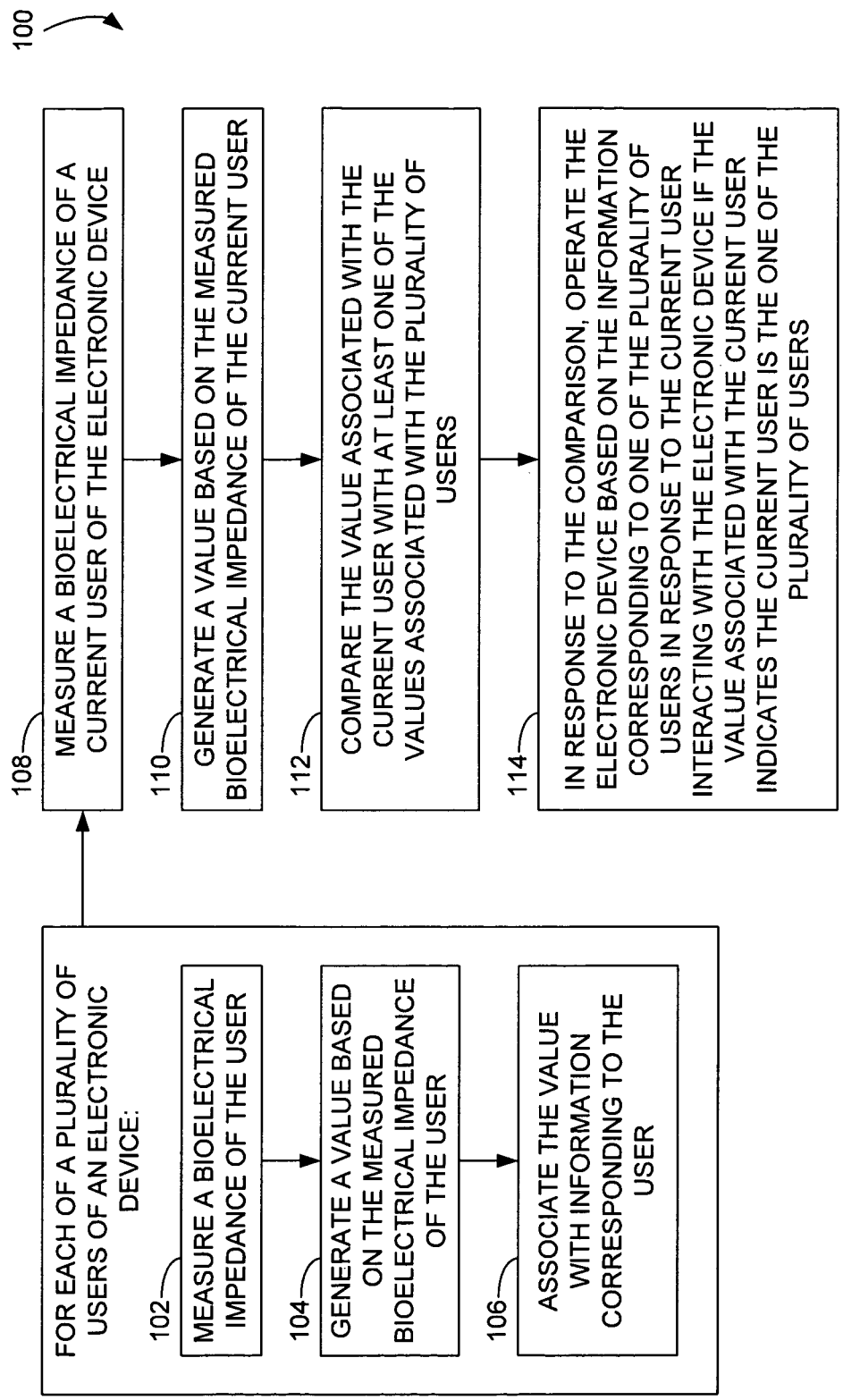
FIG. 1 is a flow diagram of a method according to an embodiment of the invention.

FIG. 1 is a flow diagram describing a method 100 according to an embodiment of the invention for identifying a user of an electronic device by way of bioelectrical impedance measurement. In the method 100, for each of a plurality of users of the electronic device, a bioelectrical impedance of the user is measured (operation 102), a value based on the measured bioelectrical impedance of the user is generated (operation 104), and the value is associated with information corresponding to the user (operation 106). This information may be any information associating the user with the operation of the electronic device.

A bioelectrical impedance of a current user of the electronic device is then measured (operation 108), and a value based on that measured bioelectrical impedance is generated (operation 110). The value associated with the current user is compared with at least one of the values associated with the plurality of users (operation 112). In response to this comparison, the electronic device is operated based on the information corresponding to one of the plurality of users in response to the current user interacting with the electronic device if the value associated with the current user indicates the current user is the one of the plurality of users (operation 114).

While FIG. 1 indicates a specific order of execution of the operations 102-114, other possible orders of execution, including concurrent execution of one or more operations, may be undertaken in other implementations. In another embodiment, a computer-readable storage medium may have encoded thereon instructions for a processor to direct the electronic device to implement the method 100.

Figure 2:
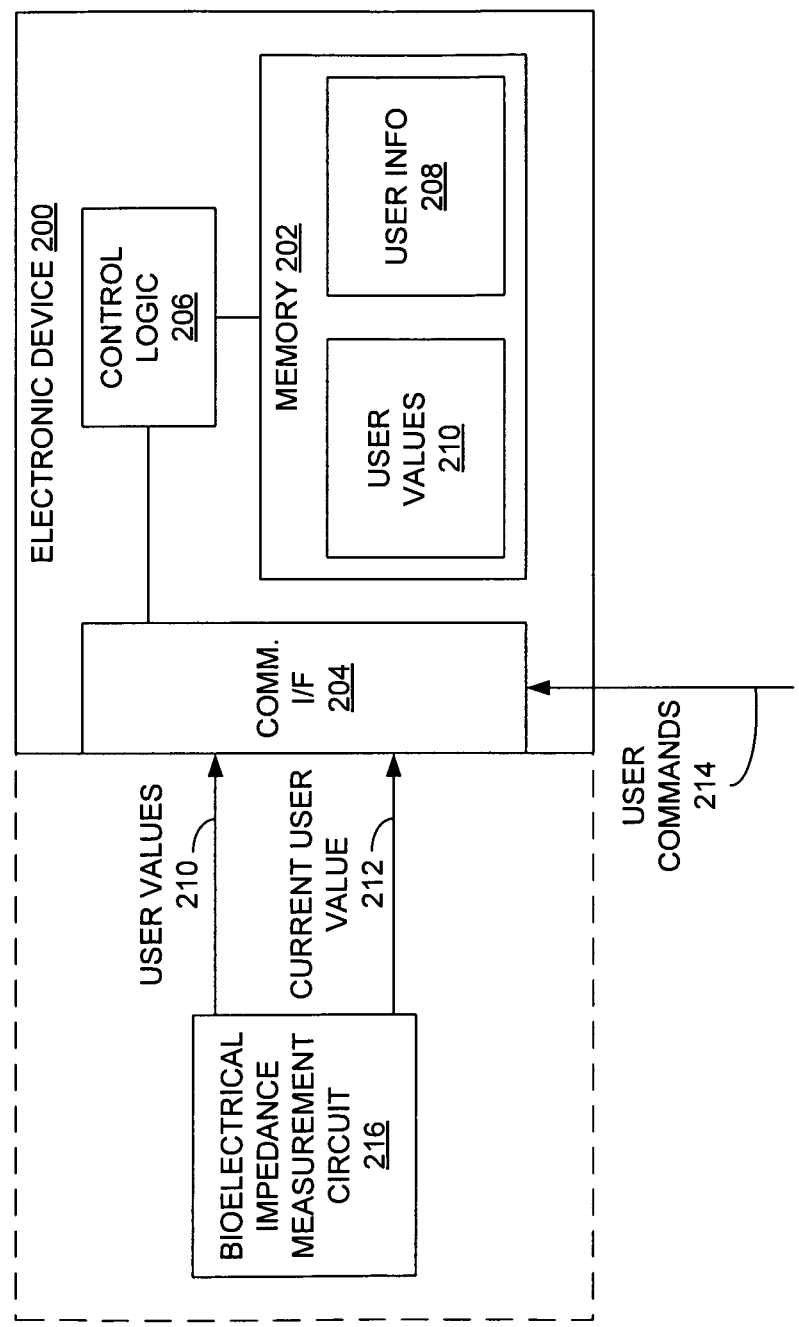
FIG. 2 is a block diagram of an electronic device according to an embodiment of the invention.

An example of an electronic device 200 capable of performing the operations of the method 100 is shown in FIG. 2. The electronic device 200 may be any electronic device in which the operation thereof is based in some part on information identified with the user of the device 200. An example of this information 208 is depicted in FIG. 2. The information 208 may be preferences or options which control the operation of the device 200 when the user is interacting with the device 200. In another implementation, the information 208 may indicate whether the identified user may access some or all of the functionality of the device 200. Other uses for the information 208 associated with the user may be employed in further implementations. Specific examples of the electronic device 200 include, but are not limited to, satellite and cable television set-top boxes, satellite radio receivers, desktop and laptop computers, personal digital assistants (PDAs), and mobile communication devices.

The electronic device 200 includes a memory 202, a communication interface 204, and control logic 206. The communication interface 204 may be any communication interface configured to receive values 210 based on measured bioelectrical impedances of users of the electronic device 200. The bioelectrical impedance of the user may be measured on any portion of the body of the user. In general, the electronic device 200 employs the values 210 based on the impedance measurements to distinguish one user of the device 200 from another.

As shown in FIG. 2, in one embodiment, the electronic device 200 may also incorporate a measurement circuit 216 configured to measure the bioelectrical impedances of the users and generate the values 210 associated with the measurements. Numerous methods for measuring human bioelectrical impedance exist, such as that discussed in U.S. Patent Application Publication No. 2006/0167374, U.S. Patent Application Publication No. 2006/0122533, U.S. Patent Application Publication No. 2005/0098343, and U.S. Patent Application Publication No. 2005/0098343, each of which is incorporated by reference herein in its entirety. While bioelectrical impedance measurements are typically employed for human body composition analysis (such as body fat percentage, body water percentage, and the like), the methods and apparatuses discussed herein utilize bioelectrical impedance measurements to distinguish one user from another.

The communication interface 204 is also configured to receive user commands 214 for the electronic device 200. The communication interface 204 may be any wired or wireless communication interface capable of receiving the user commands 214. While FIG. 2 depicts the communication interface 204 as a single interface adapted to receive both the user commands 214 as well as the values 210 based on measured bioelectrical impedances of users, the specific circuitry for receiving these values 210 may be logically and/or physically separate from the circuitry employed to receive the user commands 214.

The user commands 214 may be any commands or instructions which the electronic device 200 performs some function in response thereto. In one implementation, such commands 214 may be initiated by way of a menu system provided to the user by the electronic device 200.

The control logic 206 of the electronic device 200 may include any control circuitry capable of performing the various tasks described below. For example, the control logic may be a processor, such as a microprocessor, microcontroller, or digital signal processor (DSP), configured to execute instructions directing the processor to perform the functions enumerated below. In another implementation, the control logic 206 may be hardware-based logic, or may include a combination of hardware, firmware, and/or software elements.

The control logic 206 is coupled with a memory 202. The memory 202 may be any device or component capable of storing digital data, such as one or more integrated circuits of static random access memory (SRAM), dynamic random access memory (DRAM), flash memory, and the like. In another implementation, the memory 202 may be a magnetic or optical disk drive, or other type of storage device. Further, while the memory 202 is depicted as residing within the electronic device 200, the memory 202 may be located external to the electronic device 200 and coupled to the device 200 by way of a dedicated connection, communication network, or other communication means.

In operation, the control logic 206 is configured to, for a plurality of users, receive a value 210 based on a measured bioelectrical impedance of the user from the communication interface 204, and associate the value 210 with information 208 corresponding to the user. This user information 208 and associated user values 210 are stored in the memory 202 of the electronic device 200. The control logic 206 then receives a value 212 based on a measured bioelectrical impedance of a current user via the communication interface 204. The control logic 206 compares the current value 212 with at least one of the values 210 associated with the plurality of users. If the comparison indicates that the current user and one of the plurality of users are the same, the control logic 206 operates the electronic device 200 based on the information 208 associated with the one of the plurality of users in response to user commands 214 initiated by the current user.

Figure 3:
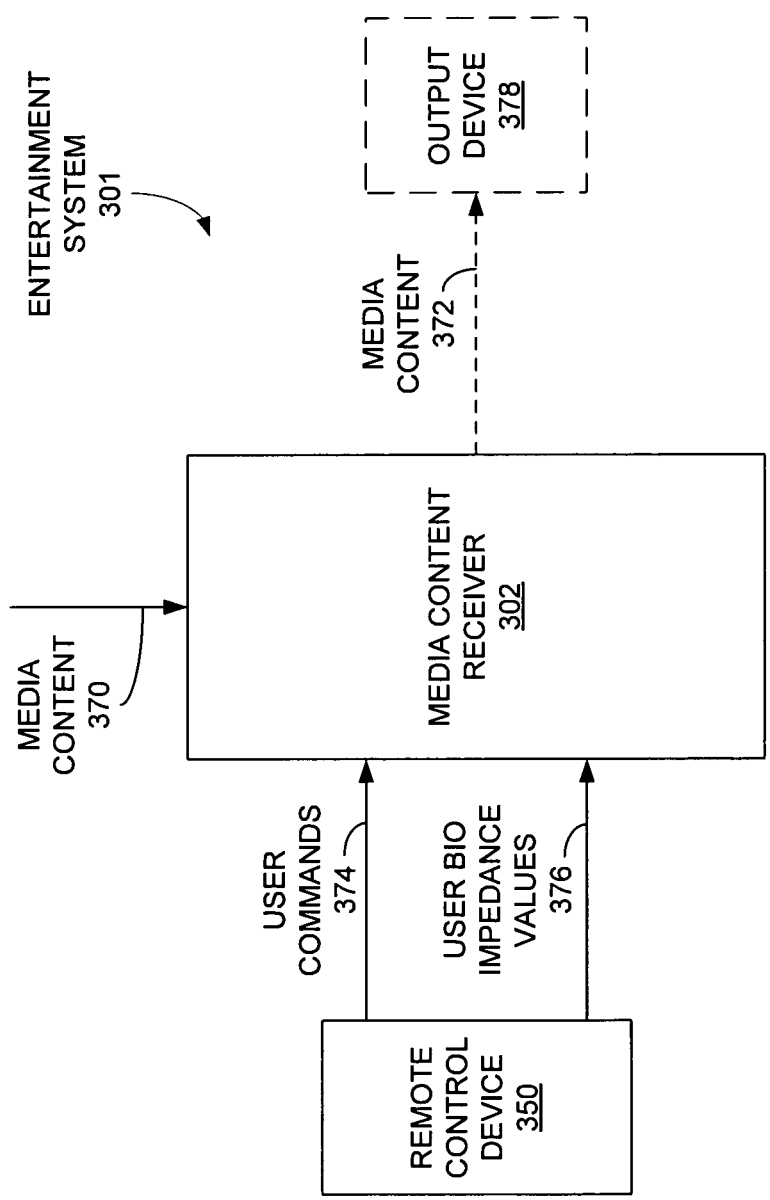
FIG. 3 is a block diagram of an entertainment system according to an embodiment of the invention including a media content receiver and an associated remote control device.

A particular example of an entertainment system 301 configured to employ the user identification method discussed above is presented in FIG. 3. The entertainment system 301 includes a media content receiver 302 and a remote control device 350 associated with the receiver 302. As shown in FIG. 3, the media content receiver 302 receives media content 370, such as audio/video programming and other content, and presents the content to a user. In one example, the media content 370 may be transmitted as media content 372 for presentation to a user by way of an output device 378, such as a television, video monitor, audio receiver, and the like.

Specific instances of the media content receiver 302 include, but are not limited to, television set-top boxes for satellite, cable, and terrestrial broadcast systems; terrestrial, cable, and satellite radio receivers; and computer systems, as well as any other device capable of receiving media content, such as audio/video programming, and presenting the content for display to a user. In the context of the embodiments discussed herein, the term "audio/video" may refer to video and associated audio, video only, or audio only. In the discussion below, the media content receiver 302 is presumed to operate as a satellite television set-top box receiver.

In addition to the media content 370, the media content receiver 302 also receives user commands 374 and user bioelectrical impedance values 376 from a remote control device 350. The remote control device 350 transmits the user commands 374 and the impedance values 376 by way of wired or wireless transmission to the media content receiver 302 for further processing. In FIG. 3, the commands 374 and values 376 are transmitted by way of ultra-high frequency (UHF) or infrared (IR) signals, as is common with remote control devices associated with television set-top boxes. However, other communication technologies, such as optical and acoustic communication technology, may be utilized to transmit the user commands 374 and the impedance values 376 in other examples.

In one embodiment, the remote control device 350 measures a bioelectrical impedance of a user, and transfers a value 376 based on that impedance to the media content receiver 302. The receiver 302 then associates the value 376 with information corresponding to the user. In the case of a satellite set-top box, the information may include, but is not limited to, a list of favorite channels specified by the user, programming recommendations for the user, parental control information associated with the user, purchase information associated with the user, and peer group information (described below) associated with the user. The information may include any other data associated with that particular user operating the receiver 302 via the commands 374 transferred from the remote control device 350 to the receiver 302.

Ultimately, each user interacting with the receiver 302 by way of the remote control device 350 may be identified with the user's own set of information maintained in the media content receiver 302 by way of a value 376 based on a bioelectrical impedance measurement of that user. As a result, when another user begins interacting with the receiver 302 through the remote control device 350, the remote control device 350 may measure the impedance of this latest user, generate a value 376 based on the impedance, and transmit the value 376 to the receiver 302. The receiver 302 may then compare this value 376 to previous values 376 to determine the identity of the latest user, and control the operation of the receiver 302 based on the information corresponding to that user.

Figure 4:
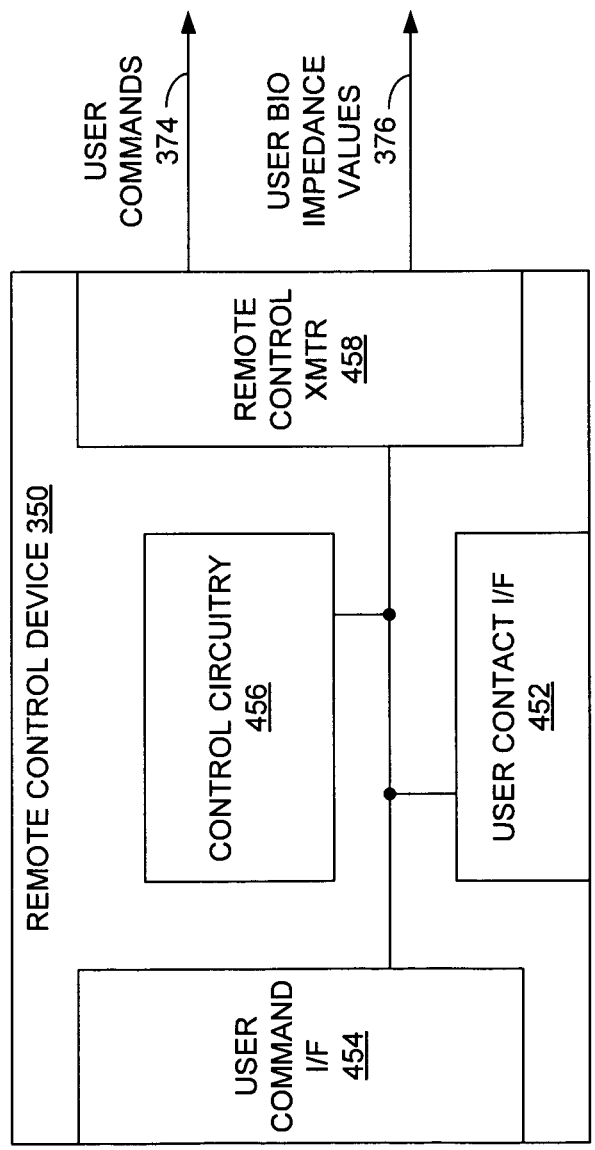
FIG. 4 is a block diagram of the remote control device of FIG. 3 according to an embodiment of the invention.

FIG. 4 provides a more detailed view of the remote control device 350 of FIG. 3. The remote control device 350 includes a user contact interface 452, a user command interface 454, control circuitry 456, and a remote control transmitter 458. Other conventional components not shown in FIG. 4 may also be incorporated into the device 350 without departing from the various aspects of the device 350 described below.

Figure 5:
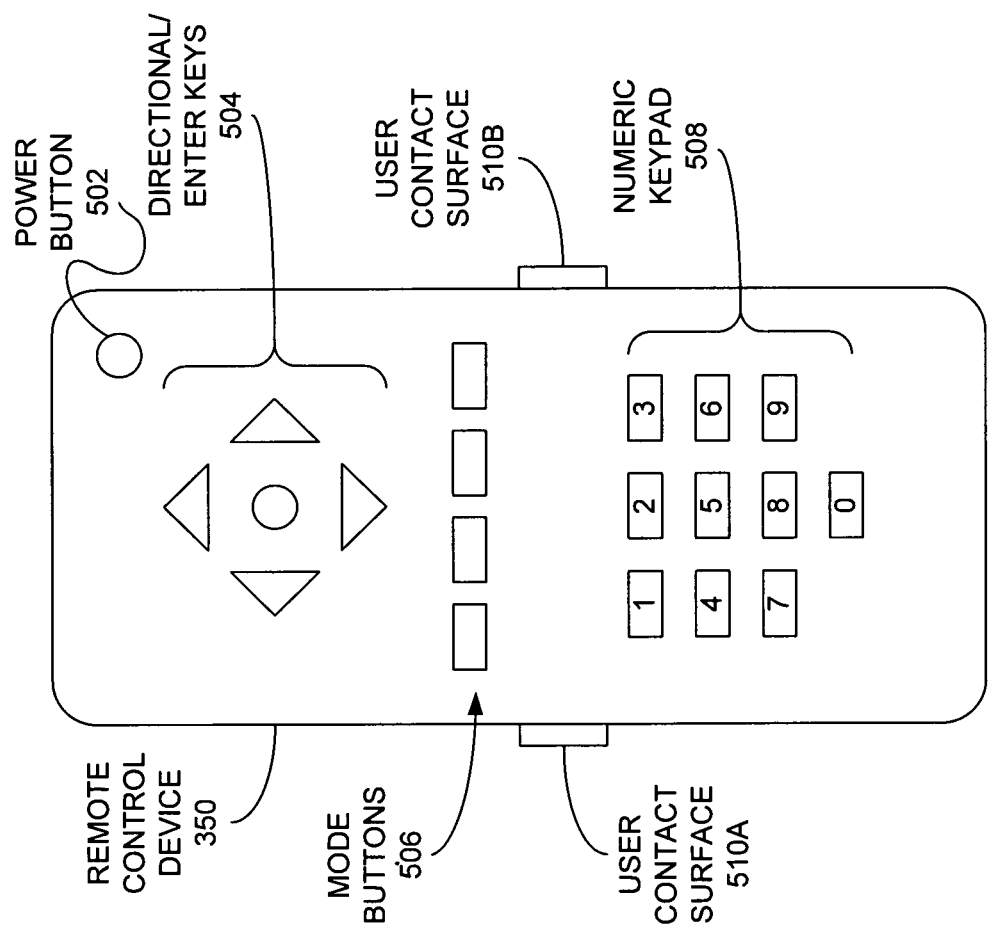
FIG. 5 is a top view of the remote control device of FIG. 3 according to an embodiment of the invention.

FIG. 5 provides a simplified top view of the example remote control device 350 of FIGS. 3 and 4. The device 350 includes a number of user input devices, such as buttons or keys, light-emitting diode (LED) indicators, and the like, that constitute the user command interface 454 of FIG. 3. More specifically, the remote control 350 of FIG. 5 includes a power button 502 for powering the media content receiver 302, and a directional key group 504 including buttons indicating "up", "down", "left", and "right", along with an "enter" key, for navigating a menu system provided by the receiver 302. Also shown are a set of mode buttons 506 for altering the mode in which the remote control device 350 is implemented. One particular type of mode may be the type of device with which the remote control 350 is communicating, such as the receiver 302, a television, an audio receiver, and so on. The user command interface 454 also includes a numeric keypad 508 having a key for each of the decimal digits "0" through "9", which may be used for channel number entry, recording timer setting, and other functions. Any of these keys may include an integrated LED indicator to signal status of the remote control device 350 to the user, such as the current mode of the device 350. Other buttons, such as channel or volume "up" and "down" keys, may be included in various implementations.

Referring to FIG. 4, the user employs the user command interface 454 to allow the user to issue user commands 374 to control various operations of the media content receiver 302, such as powering on or off the receiver 302, setting default conditions, selecting programming channels for viewing or recording, and other user-controllable functions of the receiver 302. The control circuitry 456 receives the user commands 374 issued by the user via the user command interface 454 and places them in a form for transmission to the receiver 302 before transferring the commands 374 to the transmitter 458.

The remote control transmitter 458 is configured to receive the user commands 374 from the control circuitry 456 and transmit the commands 374 to the electronic device 302. The transmitter 458 may transmit the commands 374 by wireless technology, such as by way of UHF or IR signals, as indicated above, although other communication methods, such as wired, optical, and acoustic communication technology, may be utilized in other embodiments.

FIG. 5 also depicts the user contact interface 452, which provides a physical structure through which a bioelectrical impedance of a user may be measured. The circuitry employed to measure this impedance may be incorporated within the control circuitry 456, as discussed in greater detail below. In FIG. 5, first and second user contact surfaces 510A, 510B comprise the user contact interface 452, wherein the surfaces 510A, 510B comprise an electrically conductive metal or other material. Thus, when grasping or retrieving the remote control device 350, the two user contact surfaces 510 may contact two separate areas of skin on the hand or fingers of the user, thus facilitating a measurement of the bioelectrical impedance of the user across the two areas. FIG. 5 specifically illustrates the two user contact surfaces 510 being located on opposing sides of the remote control device 350, although any other location for the contact surfaces 510 on the device 350, including on the top, bottom, or ends of the device 350, may be employed in other arrangements. Also, other portions of the body, such as the back of the hand or arm, may be exploited for the impedance measurement.

Figure 6:
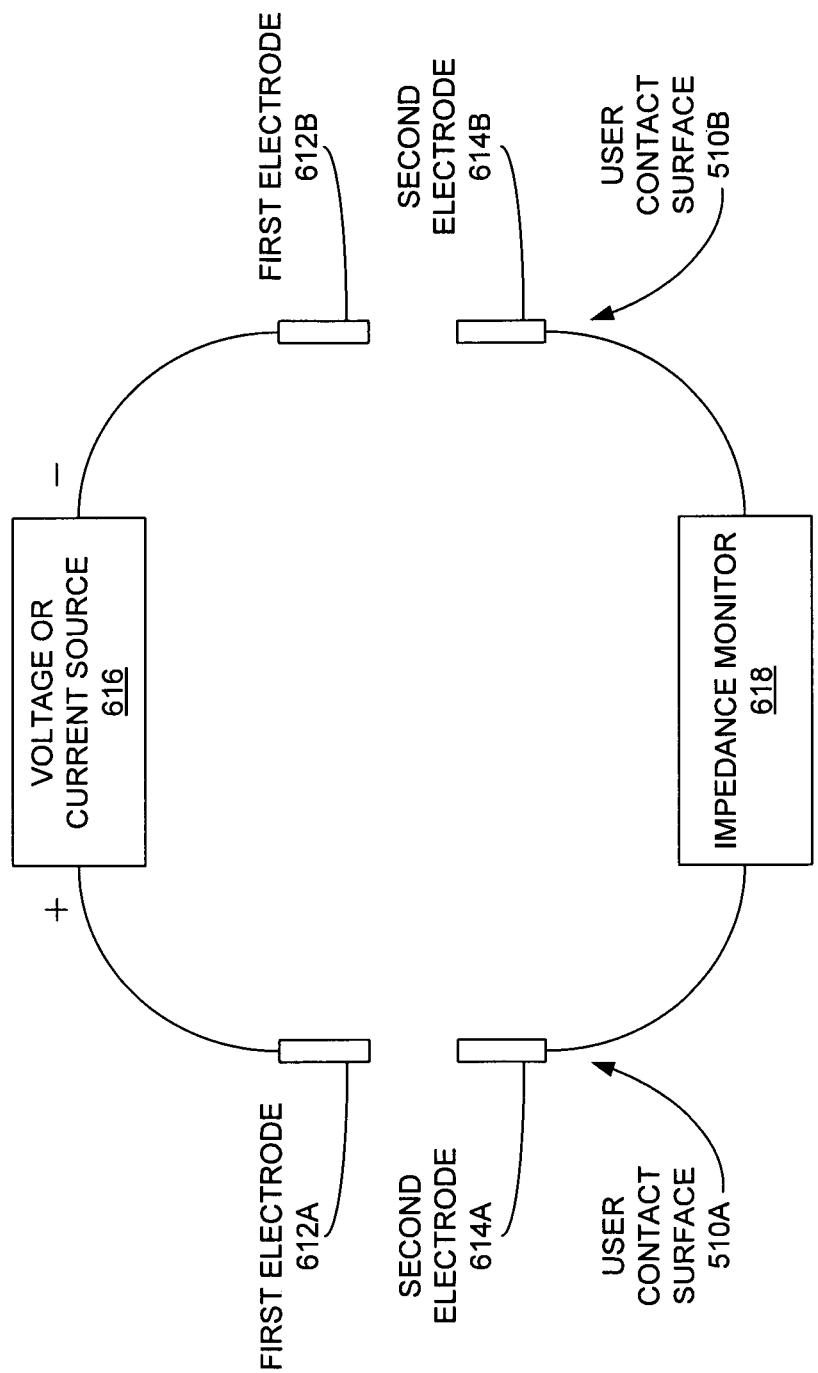
FIG. 6 is a block diagram of circuitry within the remote control device of FIG. 3 for measuring a bioelectrical impedance of a user according to an embodiment of the invention.

In the configuration of FIG. 5, only two user contact surfaces 510 are employed. For example, the contact surfaces 510 may be used to measure the impedance of the user at the two corresponding locations on the skin of the user without a separate driving signal surface to facilitate the measurement. In another implementation, more than two surfaces 510 may be located on the remote control device 350. For example, as shown in FIG. 6, each of the user contact surfaces 510 may include two separate electrodes: first electrodes 612A, 612B coupled to a voltage or current source 616 for impressing a voltage or current across the skin of the user, and second electrodes 614A, 614B coupled to an impedance monitor 618 to monitor or measure the impedance of the user while the voltage or current applied through the first electrodes 612 is being activated. In the embodiment of FIG. 4, the voltage or current source 616 and the impedance monitor 618 are incorporated within the control circuitry 456.

In general, impedance includes two components: a resistance component and a reactance (i.e., capacitance and/or inductance) component. Depending on the particular implementation, the control circuitry 456 may measure either or both of these components as the bioelectrical impedance of a user. For example, to measure the resistance component of the impedance, a direct current (DC) current source may be used as the source 616, while an alternating current (AC) current source may serve as the source 616 for a reactance measurement. To measure both resistance and reactance, both AC and DC current sources may be used in a serial fashion in conjunction with the impedance monitor 618. Other methods of measuring either or both of the resistance and the reactance may be used in other examples.

To allow the user to initiate a bioelectrical impedance measurement, the control circuitry 456 may monitor the user contact interface 452 to determine if a finite resistance is detected from one user contact surface 510 to another in one embodiment. If the control circuitry 456 detects a finite impedance, the control circuitry 456 may then initiate a more precise measurement of the impedance appearing across the user contact surfaces 510. Thus, the user may initiate the impedance measurement by merely making contact with both user contact surfaces 510A, 510B.

In another example, a user that has just grasped the remote control 350 may wish to initiate the impedance measurement to alert the receiver 302 of the desire of the user to interact with the receiver 302. To that end, the user may press one of the keys of the user command interface 454 before or while making contact with the user contact surfaces 510. In this case, the user specifically initiates the impedance measurement process to identify the user, thus precluding the possibility that inadvertent contact with the user contact surfaces 510 will cause an unnecessary or unwanted impedance measurement.

In another arrangement, the remote control device 350 may include a sensor (not shown in FIG. 3) that may detect motion, momentum, tilt, or the like, such as a mercury switch, thus sensing when a user has picked up the remote control device 350. Once the sensor detects such movement, the remote control device 350 may initiate the bioelectrical impedance measurement.

In some applications, the control circuitry 456 may determine that the measured bioelectrical impedance for a particular user should be should be ignored. For example, the measured impedance for a user may lie outside a predetermined range of acceptable impedances. For example, an insufficient amount of contact between the user and the user contact surfaces 510 may cause an extraordinarily high impedance reading that is not likely to be duplicated the next time the user impedance is measured. In response, the control circuitry 350 may indicate to the user by way of the user command interface 454 that the impedance must be measured again, and continue with a subsequent impedance measurement. In another implementation, the control circuitry 454 may indicate to the receiver 302 that the previous impedance measurement was unusable. In turn, the receiver 302 may alert the user of this status by way of a display, a connected output device, or other means.

Based on a successful impedance measurement, the control circuitry 456 generates a value 376 based on the measured bioelectrical impedance. The value 376 may take any number of forms, such as a value in ohms of the actual impedance, an integer or fractional value, or some other type of value. The control circuitry 456 then transfers the value 376 to the transmitter 458, which transmits the value 376 to the media content receiver 302.

Figure 7:
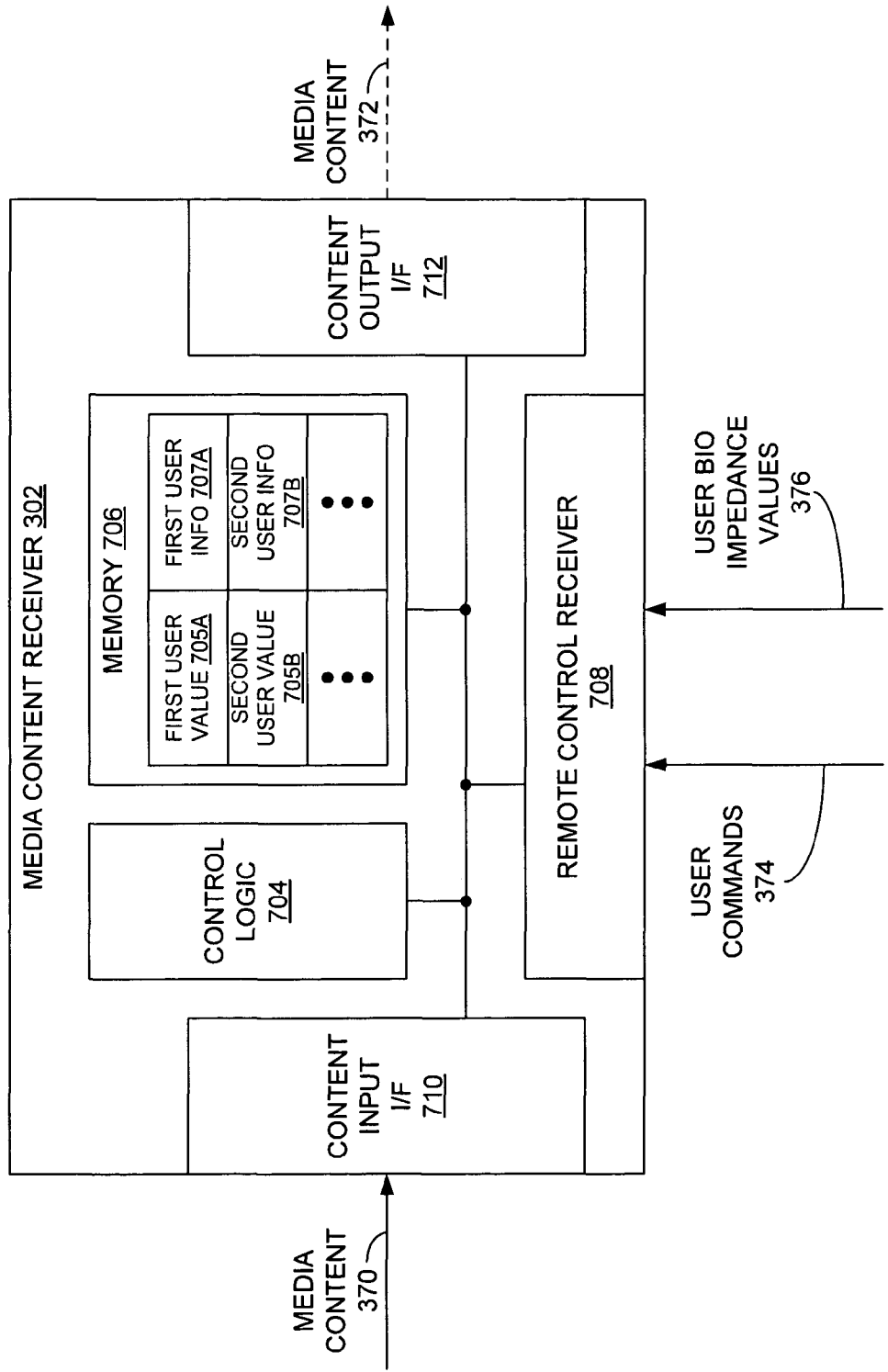
FIG. 7 is a block diagram of the media content receiver of FIG. 3 according to an embodiment of the invention.

FIG. 7 is a block diagram of the media content receiver 302 of FIG. 3, which in the present example is a satellite television set-top box. The receiver 302 includes control logic 704, a memory 706, a remote control receiver 708, a content input interface 710, and a content output interface 712. Other components often found within a satellite television set-top box, such as a digital video recorder (DVR), may be included in the receiver 302, but are not discussed herein to simplify and facilitate the following discussion.

The content input interface 710 receives the media content 370 shown in FIG. 3 for processing and eventual presentation as the output media content 372 to a user by way of the content output interface 712. In the case of a satellite set-top box, the content input interface 710 may include circuitry for receiving a satellite signal from an antenna, down-converting the signal, selecting a particular transponder frequency by way of a tuner, descrambling and/or decoding the data packets of the signal, selecting those data packets associated with a particular programming channel, and so on.

In one implementation, the incoming media content 370 may incorporate one of the Motion Picture Experts Group (MPEG) standards for data encoding and compression, such as MPEG-2 or MPEG-4. Other data formatting or encoding methods, both analog and digital, may be employed in other embodiments.

The content output interface 712 of the media content receiver 302 is configured to deliver audio/video programming to an output device (not shown in FIG. 7) for display to a user. Typically, the content output interface 712 is configured to reformat the incoming media content 370 so that the resulting output content 372 may be processed by the output device for presentation to a user. For example, the output content 372 may take the form of audio and video data suitable for transport over one or more of several audio/video connections, including, but not limited to, coaxial cable, composite video with separate audio channels, component video with separate audio channels, and the High-Definition Multimedia Interface (HDMI). Additionally, as described below, the content output interface 712 may also present information regarding the various impedance measurement values 376 being received at the receiver 302.

The remote control receiver 708 is configured to receive the user commands 374 and the bioelectrical impedance values 376 from the remote control device 350. More specifically, the remote control receiver 708 is configured to receive the signals transmitted by way of the remote control transmitter 458 of the remote control device 350. As stated above, the signals may be UHF or IR wireless signals, or communication signals propagated according to another signal technology.

Within the media content receiver 302, communicatively coupled with each of the memory 706, the remote control receiver 708, the content input interface 710, and the content output interface 712, is the control logic 704. In one embodiment, the control logic 704 may include one or more processors, such as microprocessors, microcontrollers, digital signal processors (DSPs), or any other processor configured to execute software instructions for performing the various tasks identified with the control logic 704, such as coordinating the activities of the other components of the media content receiver 302, as well as the specific operations discussed in greater detail below. The software may be stored in a memory, such as the memory 706 shown in FIG. 7, or a memory located internal to the control logic 704. In another example, the control logic 704 may be a collection of hardware logic circuitry to perform the functions described below, or a combination of software, firmware, and/or hardware elements.

In operation, the control logic 704 receives a first bioelectrical impedance measurement value 376 from the remote control receiver 708. In response, the control logic 704 may first check to determine if other impedance values have been previously received and stored in the memory 706. Presuming this impedance value 376 is indeed the first impedance value received, the control logic 704 may store the value 376 as a first user value 705A in the memory 706 and associate the value 705A with first user information 707A.

Generally, the user information 707 may be any information useful in the operation of the media content receiver 302 that is associated with, or corresponds to, a particular user. In one example, the user information 707 may include a list of favorite television channels as specified by that particular user. In another example, the user information 707 includes one or more program viewing recommendations made available by a provider of the programming, a movie critic, or other entity. Such recommendations may be based on the user's age or other demographic information. In another case, the information 707 may include parental control information, such as the identification of one or more channels selected by the user to be blocked from younger users. Further, the user information 707 may include purchase information, such as the identification of products previously purchased by the user through the receiver 302, credit card and other billing information associated with the user, and so. According to another example, the user information 707 may include "peer group" information associated with the user. In one embodiment, peer group information is information necessary to share content or otherwise communicate with other receiver 302 users identified by the original user as the peer group. In one example, the users of the peer group may all be users of the same receiver 302 of FIG. 7, or some or all of the users of the peer group may be users of other receivers 302 in communication with the receiver 302 of FIG. 7. Many other types of information associated with a particular user of the media content receiver 302 may be incorporated as part of the user information 707 in other implementations.

Any impedance value 376 received by the media content receiver 302 may be checked for validity by comparing the value 376 to a predetermined range of potential values (or to previously stored values 705, if the user is known to be a previous user), and indicating to the current user if the associated bioelectrical impedance measurement should be attempted again, similar to the method described above in connection with the remote control device 350 of FIG. 4.

In one embodiment, the most recently received impedance value 376 is identified with the current user of the media content receiver 302. Thus, user commands 374 received through the remote control receiver 708 after or concurrently with the received impedance value 376 are performed within the context of the user information 707 associated with the current impedance value 705. For example, if the user requests a favorite channels list, the list incorporated within or referenced by the user information 707 linked to the most recently received impedance value 376 is presented to the user.

The control logic 704 may also associate the name of the user with the bioelectrical impedance value in one implementation. In one example, the user may use a menu selection provided by the control logic 704 to input the name of the user by way of one or more user commands 374. In turn, the control logic 704 associates the input name with the most recently received impedance value 376. If the name has been previously input, the user may be able to select the name from a list of previously entered names in another embodiment. The name may then be presented to the user via the content output interface 712 or another communication path so that the current user may verify that the control logic 704 has correctly identified the current user.

At some point, the control logic 704 receives another bioelectrical impedance measurement value 376 by way of the remote control receiver 708. Again, this most recent impedance value 376 is compared to the previously stored impedance values (in this case, the value 705A). If the comparison indicates that the user associated with the stored value 705A is not the same user corresponding to the most recently received value 376, the control logic 704 may presume that the most recently received value 376 corresponds with a new user, and thus stores the received value 376 as a new value 705B in the memory and associates the value 705B with its own user information 707B.

In another implementation, the user may be able to employ a user command 374 or other means to indicate that the user is interacting with the receiver 302 for the first time, and thus wishes the receiver 302 to treat the impedance value 376 of this user as being new. In that case, such a user command 374 may effectively place the receiver 302 into a "learning mode" in which the receiver 302 presumes that the current impedance value 376 is to be associated with a new user. Otherwise, if the comparison between the latest value 376 and the stored value 705A signifies that the most recently received value 376 is associated with the user corresponding to the previously stored value 705A, the corresponding user information 707A is employed in the operation of the receiver 302 at least until a new impedance value 376 is received.

In another example, if the comparison indicates that the user associated with the stored value 705A is not the same user corresponding to the most recently received value 376, the control logic 704 may treat the current user as a "guest". In this instance, the control logic 704 does not attempt to store the received value 376 in the memory 706 and associate new user information 707 with the received value 376. Instead, the control logic 704 may allow the current user to operate the receiver 302 under a default set of user information. In one example, the default user information may prevent access to certain channels, prohibit purchases from the service provider via the receiver 302, and so on. Handling the current user in this manner may be appropriate under circumstances in which the current user is not expected to be interacting with the receiver 302 for more than a few days.

The comparison between different bioelectrical impedance values may be performed in a number of ways. In one example, FIG. 8A demonstrates an example of four different stored impedance values 705 associated with four users, User1 through User4. A predetermined range 802 about each impedance value 705, such as one based on a percentage of the impedance value 705 or a preset impedance difference, determines the possible received impedance values 376 that may be associated with the particular value 705 and its corresponding user information 707. As a result, many possible receiver values 376 located between the ranges 802 may not be associated with any particular stored value 705, thus possibly requiring a re-measurement of the impedance of the current user, or indicating that the user is a new user.

In some cases, the ranges of two or more adjacent stored values 705 overlap, in which a newly received value 376 may be identified with both of the nearby values 705. To address this possibility, the control logic 704 may display the user name of each stored value 705 in question, and allow the user to select the appropriate name by way of the user commands 374.

In an alternative arrangement, the control logic 704 may select boundaries between each stored value 705 that reduce or eliminate the possibility of a newly received value 376 not being associated with one of the stored values 705. FIG. 8B shows one such implementation, in which the range 804 for each of the user values 705 is expanded so that fewer received impedance values 376 not associated with a previously stored impedance value 705 are possible. Such an implementation may be possible if the remote control device 350 or the receiver 302 is capable of distinguishing between impedance values for existing, as opposed to new, users. In yet another example, if the received impedance value 376 is known to be associated with a previous user, the current user may simply be associated with the user information 707 corresponding to the closest stored impedance 705.

In one implementation, the control logic 704 may determine that a received impedance value 376 associated with one of the stored impedance values 705 may provide a better representative value for the current user against which future received values 376 may be compared. As a result, the control logic 704 may replace the stored impedance value 705 for the current user with the received value 376 in such a situation.

Various embodiments as described herein for identifying a user of an electronic device may provide a number of benefits. In general, bioelectrical impedance measurement, normally associated with body composition analysis and the like, is employed as an automatic means for identifying a current user from among two or more potential users. As a result, modes of operation of the electronic device that depend at least in part on an accurate identification of the current user may be accomplished without requiring the user to explicitly indicate the identity of the current user to the device. Instead, by merely grasping a remote control device or other component associated with the electronic device, or even a portion of the electronic device itself, such that the bioelectrical impedance measurement of the user may take place, the electronic device may identify the user quickly and automatically without further user intervention.

While several embodiments of the invention have been discussed herein, other embodiments encompassed by the scope of the invention are possible. For example, while various embodiments have been described primarily within the context of satellite set-top boxes, any other electronic device whose operation depends at least in part on an identification of the user, such as cable and terrestrial set-top boxes; satellite, cable, and terrestrial radio receivers; DVRs; and various computer and communication systems, may benefit from application of the various concepts described herein. In addition, aspects of one embodiment disclosed herein may be combined with those of alternative embodiments to create further implementations of the present invention. Thus, while the present invention has been described in the context of specific embodiments, such descriptions are provided for illustration and not limitation. Accordingly, the proper scope of the present invention is delimited only by the following claims and their equivalents.

What is claimed is:

1. A method of identifying a user of an electronic device, the method comprising:
for each of a plurality of users of the electronic device:
measuring a bioelectrical impedance of the user;
generating a value based on the measured bioelectrical impedance of the user; and
associating the value with information corresponding to the user;
measuring a bioelectrical impedance of a current user of the electronic device;
generating a value based on the measured bioelectrical impedance of the current user;
comparing the value associated with the current user with at least one of the values associated with the plurality of users;
replacing the value associated with the one of the plurality of users with the value associated with the current user when the value associated with the current user indicates that the current user is the one of the plurality of users; and
in response to the comparison, operating the electronic device based on the information corresponding to one of the plurality of users in response to the current user interacting with the electronic device if the value associated with the current user indicates the current user is the one of the plurality of users.

2. The method of claim 1, wherein:
measuring the bioelectrical impedance of the user comprises measuring a resistance of the user.

3. The method of claim 1, wherein:
measuring the bioelectrical impedance of the user comprises measuring a reactance of the user.

4. The method of claim 1, wherein:
measuring the bioelectrical impedance of the user comprises measuring a bioelectrical impedance across two locations on a hand of the user.

5. The method of claim 1, wherein:
the electronic device comprises a media content receiver.

6. The method of claim 5, wherein:
the information corresponding to the user comprises a favorite channels list associated with the user.

7. The method of claim 5, wherein:
the information corresponding to the user comprises programming recommendations for the user.

8. The method of claim 5, wherein:
the information corresponding to the user comprises parental control information associated with the user.

9. The method of claim 5, wherein:
the information corresponding to the user comprises purchase information associated with the user.

10. The method of claim 5, wherein:
the information corresponding to the user comprises peer group information associated with the user.

11. The method of claim 1, wherein:
the value associated with the current user indicates the current user is the one of the plurality of users if the value associated with the current user is within one of a predetermined difference and a predetermined percentage of the value of the one of the plurality of users.

12. The method of claim 1, wherein:
the value associated with the current user indicates that the current user is the one of the plurality of users if the value associated with the current user is closer to the value associated with the one of the plurality of users than to the value associated with any other one of the plurality of users.

13. The method of claim 1, further comprising:
re-measuring the bioelectrical impedance of the user if the value associated with the user resides outside a predetermined range.

14. The method of claim 1, further comprising:
re-measuring the bioelectrical impedance of the current user if the value associated with the current user resides outside a range associated with the values associated with the plurality of users.

15. The method of claim 1, further comprising:
receiving an indication from the current user that the current user is not one of the plurality of users; and
in response to receiving the indication, associating the value associated with the current user with information corresponding to the current user.

16. The method of claim 1, further comprising:
in response to the comparison, operating the electronic device based on default information in response to the current user interacting with the electronic device if the value associated with the current user indicates the current user is not the one of the plurality of users.

17. The method of claim 1, further comprising:
in response to the comparison, associating the value associated with the current user with information corresponding to the current user if the value associated with the current user indicates the current user is not the one of the plurality of users.

18. An electronic device, comprising:
a memory;
a communication interface configured to receive values based on measured bioelectrical impedances of users of the electronic device, and to receive user commands for the electronic device; and
control logic configured to:
   for each of a plurality of users:
      receive a value based on a measured bioelectrical impedance of the user from the communication interface; and
      associate the value with information stored in the memory corresponding to the user, wherein the information includes peer group information associated with the user that indicates other users with whom to communicate;
   receive a value based on a measured bioelectrical impedance of a current user from the communication interface;
   comparing the value associated with the current user with at least one of the values associated with the plurality of users; and
   in response to the comparison, control the operation the electronic device based on the information corresponding to one of the plurality of users in response to user commands initiated by the current user if the value associated with the current user indicates the current user is the one of the plurality of users.

19. The electronic device of claim 18, further comprising:
a content input interface configured to receive media content; and
a content output interface configured to present the received media content to a user;
wherein the control logic is further configured to control the content input interface and the content output interface based on the information corresponding to the current user when the current user is interacting with the electronic device.

20. The electronic device of claim 19, wherein:
the information corresponding to the current user further comprises at least one of a favorite channels list associated with the current user, programming recommendations for the current user, parental control information associated with the current user, and purchase information associated with the current user, and peer group information associated with the current user.

* * * * *